US006694299B1

(12) United States Patent
Barrer

(10) Patent No.: US 6,694,299 B1
(45) Date of Patent: Feb. 17, 2004

(54) METHOD OF IMPLEMENTING A CARDIAC EMERGENCY READINESS PROGRAM

(76) Inventor: Matthew Barrer, 1173 Beukshire Blvd., Wyomissing, PA (US) 19610

( * ) Notice: Subject to any disclaimer, the term of this patent is extended or adjusted under 35 U.S.C. 154(b) by 0 days.

(21) Appl. No.: 09/924,503

(22) Filed: Aug. 9, 2001

Related U.S. Application Data

(60) Provisional application No. 60/255,062, filed on Dec. 14, 2000.

(51) Int. Cl.⁷ .............................................. G06F 17/60
(52) U.S. Cl. .............................................. 705/8; 705/2
(58) Field of Search ............................................ 705/8

(56) References Cited

U.S. PATENT DOCUMENTS

| | | | |
|---|---|---|---|
| 5,658,316 A | 8/1997 | Lamond et al. | |
| 5,800,460 A | 9/1998 | Powers et al. | |
| 5,853,292 A | 12/1998 | Eggert et al. | |
| 5,856,929 A | 1/1999 | McClendon et al. | |
| 6,438,417 B1 * | 8/2002 | Rockwell et al. | 607/5 |
| 6,443,735 B1 * | 9/2002 | Eggert et al. | 434/262 |

FOREIGN PATENT DOCUMENTS

WO   WO 91/19452   * 12/1991   ........... A61B/5/044

OTHER PUBLICATIONS

Obertots, Richard. "Medical Emergency Preparedness Check List for Professional Meeting Planners", Medical Meetings, Jul. 1, 2000. Downloaded from www.medicalmeetings.net.*
Chinappi, Anna. "Code Blue: Are You Prepared?" Medical Meetings. Aug. 1, 2000. Donwloaded from www.medicalmeetings.net.*
www.meetingmed.com. Dec. 1, 1999. Downloaded from www.meetingmed.com/articlearchive.*
www.safemeetings.com. Oct. 12, 1999. Downloaded from www.archive.org/www.safemeetings.com.*
Becker, Linda: Mickey Eisenberg; Carol Fahrenbruch; Leonard Cobb. "Public Locations of Cardiac Arrest: Implications for Public Access Defibrillation." New York. Jun. 2, 1998*
Riddle, Kenneth. "AEDs Increase Odds in Las Vegas, Casinos, Hotels". Fire Chief. Atlanta. Jun. 1998.*
Shelton, Deborah. "Defibrillators Increasingly Available—and Being Used". AMNews. May 15, 2000.*
Fitzenberger, Jennifer. "State Gives Law Officers Defibrillators to Save More Lives". Star Tribune. Minn. Dec. 31, 1998.*
"Complient Launches New Emergency Medical Response System" PR Newswire. May 8. 2000. pp. 3.*
"Amtrak Couples with Complient to Save Train Passenger Lives" PR Newswire. Sep. 25, 2000. pp. 3.*
Tadjer, Rivka. "Better Medicine: Health–care Providers Look to the Net". Informationweek. Mar. 6, 2000. pp. 5.*
"Heartstream: Mirage Resorts Equips Security Personnel with Life–Saving Defibrillators for Treating Victims of Sudden Cardiac Arrest". BusinessWire. 1999.*

(List continued on next page.)

*Primary Examiner*—Tariq R. Hapiz
*Assistant Examiner*—Rebecca M. Bachner
(74) *Attorney, Agent, or Firm*—Blank Rome, LLP

(57) ABSTRACT

The method of the present invention provides for the implementation of a cardiac emergency readiness program that aids victims of sudden cardiac arrest. The program includes assistance in purchasing automatic external defibrillators (AEDs), placement and training on the use of AEDs, and development of legal and public relations support plans. The method provides a complete cardiac emergency program that covers all aspects of implementing and monitoring the program. Individuals and organizations who implement the program can offer their patrons the advantage of quick and competent response to cardiac arrest emergencies.

24 Claims, 2 Drawing Sheets

OTHER PUBLICATIONS

Cate. Molly. "First Aid: Frontline Safety bets on Heart Device". Nashville Business Journal. Dec. 1, 2000.*

Dallas American Red Cross. www.archive.org/redcrossdallas.org. Aug. 23, 2000—Jan. 1, 2001.*

Website <www.premedics.com>: Company History printout pp. 1–2 included. Viewed and printed on Nov. 7, 2002.

Website <complient.com>: Home page printout included. Viewed and printed on Nov. 7, 2002.

* cited by examiner

FIG. 2

SCHEDULE "A" LOCATIONS
See Attached Sheet for any Additional Locations

| LOCATION 1 | LOCATION 2 | LOCATION 3 |
|---|---|---|
| Name: | Name: | Name: |
| Address: | Address: | Address: |
| City, State, Zip: | City, State, Zip: | City, State, Zip: |
| Contact: | Contact: | Contact: |
| Phone: | Phone: | Phone: |
| Number of Units: | Number of Units: | Number of Units: |
| Price for 1st Year: $ | Price for 1st Year: $ | Price for 1st Year: $ |
| Price per year after 1st Year: $ | Price per year after 1st Year: $ | Price per year after 1st Year: $ |
| LOCATION 4 | LOCATION 5 | LOCATION 6 |
| Name: | Name: | Name: |
| Address: | Address: | Address: |
| City, State, Zip: | City, State, Zip: | City, State, Zip: |
| Contact: | Contact: | Contact: |
| Phone: | Phone: | Phone: |
| Number of Units: | Number of Units: | Number of Units: |
| Price for 1st Year: $ | Price for 1st Year: $ | Price for 1st Year: $ |
| Price per year after 1st Year: $ | Price per year after 1st Year: $ | Price per year after 1st Year: $ |

METHOD OF IMPLEMENTING A CARDIAC EMERGENCY READINESS PROGRAM

REFERENCE TO RELATED APPLICATION

The present application claims the benefit of U.S. Provisional Application No. 60/255,062, filed Dec. 14, 2000. The disclosure of the provisional application is hereby incorporated by reference in its entirety into the present disclosure.

FIELD OF INVENTION

The present invention is directed towards a method of implementing a Cardiac Emergency Readiness ("CER") program that assists victims of sudden cardiac arrest, the program comprises surveying a location to determine the need for Automatic External Defibrillators (AEDs), assisting in purchasing and installing the AEDs, preparing an emergency response plan and providing support services, such as assisting in preparing a legal and public relations support plan.

BACKGROUND OF THE INVENTION

Everyday over 1,000 Americans die of sudden cardiac arrest. In order to prevent some of these deaths, several organizations have trained their staff in cardiopulmonary resuscitation ("CPR") to provide aid to those having heart attacks. However, CPR saves lives in less than 5% of these situations. Furthermore, after 4–6 minutes irreversible damage or death can occur and studies have shown that by the time paramedics arrive, it is often too late to resuscitate most heart attack victims.

As a result, many organizations are now proactively addressing the issue of sudden cardiac arrest by purchasing AEDs, which are devices that jolt the heart with electricity to restart the heart's beating.

Several AEDs on the market are designed to be used by non-medical personnel. These devices are simple to use, incorporating such user-friendly features as voice prompting during the operation of the device, and safety mechanisms that prevent the device from injuring a heart attack sufferer. When tested with third graders, 90% of them were able to satisfactorily operate the AEDs. Besides the ease of use, the price of AEDs has dropped in recent years and has become affordable to a wide range of individuals and institutions. The technology has made it possible for lay personnel to safely and effectively administer assistance to cardiac arrest victims in almost any surrounding.

SUMMARY OF INVENTION

The invention is directed to a method for installing a turnkey cardiac emergency readiness program that allows lay personnel to aid victims of cardiac arrest and prevent serious injury or death. The program comprises assistance in every facet of implementing the program, including purchasing, placement, and training on the use of AEDs, helping to develop an emergency response plan designating the duties of on-site personnel, providing legal and public relations support related to the program, and an indemnification plan in case of a lawsuit. The program may also certify that the individual or organization has implemented the cardiac emergency program, informing the public that the site is prepared to handle a cardiac arrest emergency.

BRIEF DESCRIPTION OF THE DRAWINGS

FIG. 2 shows a location schedule for tracking the cardiac emergency readiness program of the present invention.

DETAILED DESCRIPTION OF THE PREFERRED EMBODIMENTS

Figure 1:
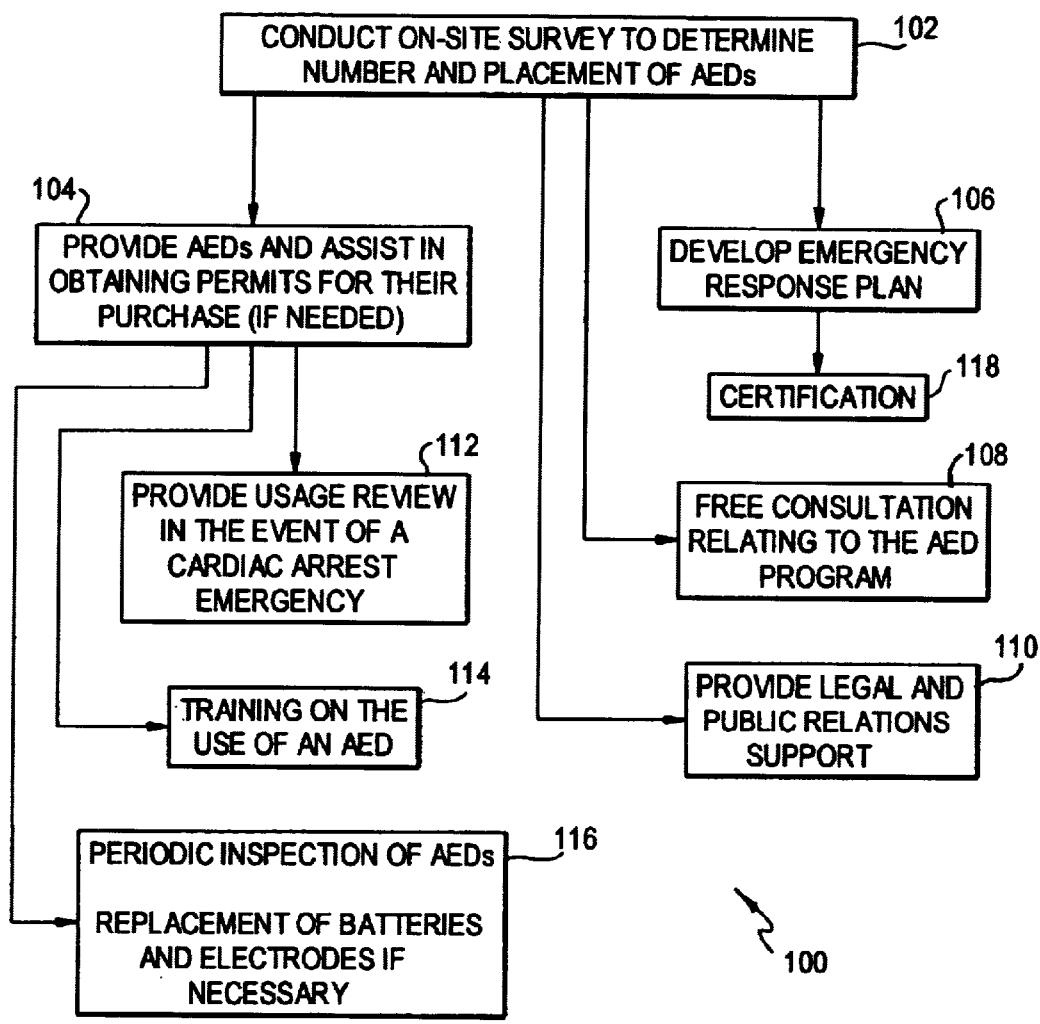
FIG. 1 is a flowchart showing the steps in the method of implementing a cardiac emergency readiness program of the present invention.

The present invention is directed towards a method of implementing a Cardiac Emergency Readiness ("CER") program. The program comprises supplying automatic external defibrillators ("AED") to individuals and institutions, and implementing a comprehensive cardiac emergency response plan.

Because AEDs have become easy to use and affordable, it is contemplated that the method of the present invention be implemented in a variety of locations, including, but not limited to:

Shopping Malls
Golf Courses
Hotels
Sporting Events
Concerts
Health Clubs
Business Complexes
Industrial and manufacturing facilities
Airports
Amusement Parks
Ski resorts
Convention Halls
Schools and Universities
Public transportation (trains, cars, buses, airplanes, boats, cruise ships, etc.)

In addition, any organization where emergency medical services cannot be on location within 4–6 minutes of a sudden cardiac arrest would benefit from implementing the program. After 4–6 minutes, the odds of resuscitating a cardiac arrest victim or other favorable outcome is greatly diminished, with the chances of survival reduced 7–10% for each minute of delay.

The method of the present invention is designed to provide a turnkey solution to implementing and maintaining a comprehensive CER program, starting from the initial purchase of the AEDs and extending to every facet of supporting the program, including public relations support and legal support.

FIG. 1 shows a flow chart 100 outlining the steps in implementing a preferred embodiment of the CER program. Initially, the program calls for conducting a site survey 102 of the premises to determine the need for AEDs, and if appropriate, the number of AEDs and optimal placement of each AED on the premises. It is generally recommended that AEDs be placed within a three-minute response time of any location, since irreversible damage can occur after that time period.

Most states require medical direction or a prescription for the purchase and use of an AED. The program helps an individual or institution handle the medical authorization process 104 by assisting in obtaining all of the necessary state and local permits for the purchase and use of the AED.

The program then develops a customized emergency response plan 106 that specifies how to deal with incidents of sudden cardiac arrest. The plan includes contacting local emergency personnel to familiarize them with the CER program. The plan provides details, such as who should contact an emergency medical specialist ("EMS"), who is qualified to use the AED, and who should meet the ambulance.

The program also provides training 114 to the personnel who will use the AED. The training is offered by instructors from the program or through certified instructors from various other organizations such as the American Heart Association or American Red Cross.

After the AEDs are in place, the program provides periodic inspections 116 to ensure the AEDs are operational and accessible and that trained personnel are stationed nearby. The inspections of the AEDs will check its overall condition, including its electrodes and batteries. In addition to or in place of inspection by an employee of the CER program, an employee of the program will contact a designated person at the site on a periodic basis to ensure the AEDs have been inspected and trained personnel are available.

The program also provides replacement of all supplies needed for the operation of the AEDs, including its electrodes and batteries 116. The supplies are provided either free or at cost depending on the nature of the program. The electrodes have a shelf life, unopened, of approximately two years and are replaced if found to be defective or worn. Similarly, if a battery fails or becomes worn, a replacement battery is provided.

In the event of a cardiac arrest or other emergency, the program provides an AED usage review 112 to ensure that it has functioned properly and is still in working condition. As part of the review, the program may also offer an evaluation of the emergency to help improve the response of personnel involved. The evaluation would include, in part, analyzing the performance of the personnel participating in the program, the adequacy of the training, the procedures used during the emergency, and the placement of the AED's. Additionally, counseling may be provided to victims and their families to help cope with the emotional trauma of the event.

The program also provides various other support services, such as helping to develop a public relations and a legal support plan 110. The public relations plan is aimed at generating goodwill towards the individual or institution implementing the CER program. It includes preparing a public relations announcement informing the public of the CER program. It provides guidance in recruiting volunteers to participate in the program and guidance on preparing newsletters discussing the CER program and other general health related information.

The program also provides legal advice and information to help limit the liability of the individual or institution and to ensure that they are in compliance with all legal requirements associated with the CER program, and in particular the use of the AEDs. For example, information on local "Good Samaritan" laws that limit the liability of persons rendering assistance to injured victims, and laws relating to the technical requirements of the AEDs and persons qualified to use the AEDs are provided. However, in the event that a lawsuit is brought against the individual or institution, the program provides litigation support in the form of references to legal counsel and expert written legal opinions on the proper jurisdictional standard of care on the use of an AED. For customers requiring additional assurance, the program offers an Indemnification Plan to indemnify the AED owner, employees and others against claims regarding proper use of the AED. In such a case, the program coordinates with the individual's or institution's insurance carrier to ensure proper liability coverage. As an added benefit, a life insurance policy covering victims of cardiac arrest on the premises may be provided.

Throughout participation in the program, free consultation 108 by email or other means is provided to answer any questions or concerns related to the use of the AEDs or the program itself.

After purchasing the AEDs and implementing the program, the individual or institution is certified 118 as having met the standards of the program. The certification informs the public that the individual or institution has established an effective cardiac arrest program that could potentially save their lives.

A second embodiment of the invention provides a method for implementing the CER program as described above, without the auditing steps included in the preferred embodiment. In other words, the program assists in setting up the CER program, but does not continually monitor the maintenance of the program. The method of the second embodiment comprises the same steps as the preferred embodiment with the omission of the certification step 118, and the periodic inspection and replacement of parts step 116. As with the method of the preferred embodiment, the supplies may be provided free or at cost depending on the nature of the program.

FIG. 2 shows a location schedule 200 that assists in tracking an individual's or institution's CER program. The chart 200 has multiple location boxes 210 that contain information relating to each site where AEDs are located. The location box contains the name of the person responsible for the AED 212, the address 214 where the AED is located, the contact person 216 who is authorized to use the AED, the phone number 218 where the contact person can be reached, and the number of AEDs at the site 220. The chart 200 is provided for illustrative purposes, and is not meant to limit the scope or breadth of the invention. The chart may be modified to include more information, or omit information without departing from the scope of the invention.

It should be understood that the sequence of steps shown in FIG. 1, illustrate a preferred embodiment of the steps of the invention. However, the steps may be performed in a variety of sequences depending on the circumstances involved. For example, if the procedure for obtaining permits for the purchase and use of an AED is a long and protracted process, one could initiate this process before conducting an on-site survey to determine the number of AEDs needed. Also, training may be provided on AEDs that are loaned to the premises for the exclusive purpose of training, before the procurement of permits or the purchase of the AEDs. Also certain steps shown in FIG. 1 may be omitted without departing from the scope of the invention, as exemplified by the second embodiment.

The program is also designed to be implemented by current owners of AEDs. The program allows current owners to implement all aspects of the AED program, other than those related to the purchase of an AED, and certifies them as having met the standards set out in the program. Current owners of an AED are able to reduce the costs incurred to set up the program by already having purchased AEDs.

Besides the obvious tangible benefits of the program, there are several intangible benefits which focus on the branding aspects of the program. Specifically, customers receive a certification seal, which clearly distinguishes the facility as being ready to deal with incidents of sudden cardiac arrest.

The program provides an important service for individuals and companies to offer their patrons who then have the comfort of knowing that the site is capable of handling cardiac emergency situations. For example, hotels can market this service to their senior citizens, in the hopes that eventually, senior citizens may choose their hotels, based in part, on the certification program. The benefits of the program will prompt many businesses to proudly display their certification seal.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method of providing a cardiac arrest emergency program comprising:

providing a customer with a single source for a comprehensive cardiac emergency program for implementing the use of automatic external defibrillators in public buildings, comprising developing, implementing and supporting the emergency program so that acquisition, placement and support of at least one automatic external defibrillator is provided with said program;

said step of developing said emergency program includes conducting a survey of the customer's premises to determine at least one location for placement of said at least one automatic external defibrillator;

said step of implementing said emergency program includes assisting in the placement of said at least one automatic external defibrillator in said at least one location determined in the survey; and said step of supporting said emergency program includes providing on-going support of said at least one automatic external defibrillator through a communication network.

2. The method of providing a cardiac arrest emergency program of claim 1, wherein:

the step of implementing said emergency program further includes selling the at least one automatic external defibrillator.

3. The method of providing a cardiac arrest emergency program of claim 1, wherein:

the step of developing said emergency program further includes assisting in complying with applicable laws relating to the use of automatic external defibrillators; and the step of supporting said emergency program further includes updating the program to respond to any new laws or changes in the applicable law.

4. The method of providing a cardiac arrest emergency program of claim 1, wherein:

the step of developing said emergency program further includes selecting personnel to serve as liaisons with emergency medical specialists who are called to the customer's premises; and the step of implementing said emergency program further includes training the customer's personnel regarding proper use of the at least one automatic external defibrillator.

5. The method of providing a cardiac arrest emergency program of claim 1, wherein:

the step of supporting said emergency program further includes providing a public relations support plan that assists in informing the public of the customer's implementation of the emergency program to promote the goodwill of the customer's business.

6. The method of providing a cardiac arrest emergency program of claim 1, wherein:

the step of supporting said emergency program further includes providing an automatic external defibrillator usage review in the event of a cardiac incident.

7. The method of providing a cardiac arrest emergency program of claim 1, wherein:

the step of supporting said emergency program further includes conducting periodic quality assurance inspections to ensure the proper operation of the at least one automatic external defibrillator.

8. The method of providing a cardiac arrest emergency program of claim 1, further comprising the step of:

collecting a fee from the customer for developing, implementing and supporting said emergency program.

9. A method of providing a personalized cardiac arrest emergency program comprising:

agreeing to provide a customer with a cardiac arrest emergency program;

providing the customer with a single source comprehensive cardiac arrest emergency program, including developing a personalized emergency program for the customer's premises that includes surveying the customer's premises for determining the proper placement of at least one automatic external defibrillator;

implementing the personalized emergency program at the customer's premises, including assisting in placing the at least one automatic external defibrillator at one or more locations on the customer's premises and certifying that the customer's premises is participating in the emergency program and has undergone a predetermined process to implement the emergency program; and supporting the personalized emergency program by providing on-going support for the emergency program during the time that the customer is participating in the emergency program including support through a communication network.

10. The method of providing a cardiac arrest emergency program of claim 9, wherein:

the step of implementing said emergency program further includes selling the at least one automatic external defibrillator.

11. The method of providing a cardiac arrest emergency program of claim 9, wherein:

the step of developing said emergency program further includes assisting in complying with applicable laws relating to the use of automatic external defibrillators; and the step of supporting said emergency program further includes updating the program to respond to any new laws or changes in the applicable law.

12. The method of providing a cardiac arrest emergency program of claim 9, wherein:

the step of developing said emergency program further includes selecting personnel to serve as liaisons with emergency medical specialists who are called to the customer's premises; and the step of implementing said emergency program further includes training the customer's personnel regarding proper use of the at least one automatic external defibrillator.

13. The method of providing a cardiac arrest emergency program of claim 9, wherein:

the step of supporting said emergency program further includes providing a public relations support plan that assists in informing the public of the customer's implementation of the emergency program to promote the goodwill of the customer's business.

14. The method of providing a cardiac arrest emergency program of claim 9, wherein:

the step of supporting said emergency program further includes providing an automatic external defibrillator usage review in the event of a cardiac incident.

15. The method of providing a cardiac arrest emergency program of claim 9, wherein:

the step of supporting said emergency program further includes conducting periodic quality assurance inspections to ensure the proper operation of the at least one automatic external defibrillator.

16. The method of providing a cardiac arrest emergency program of claim 9, further comprising the step of:

collecting a fee from the customer for developing, implementing and supporting said emergency program.

17. A method of providing a cardiac arrest emergency program comprising:

providing a customer with a single source for a cardiac emergency program comprising developing a cardiac emergency program for using at least one automatic external defibrillator which includes conducting a survey of the customer's premises to determine at least one location for the placement of said at least one automatic external defibrillator and preparing a plan of action in case of a cardiac arrest on the customer's premises;

implementing the emergency program by assisting in the placement of the at least one automatic external defibrillator and instructing the customer on the plan of action; and supporting the emergency program by providing on-going support for the at least one automatic external defibrillator to ensure the proper operation of said at least one automatic external defibrillator, and updating said plan of action as the customer's needs change, wherein said supporting the emergency program includes support through a communication network.

18. The method of providing a cardiac arrest emergency program of claim 17, wherein:

the step of implementing said emergency program further includes selling the at least one automatic external defibrillator.

19. The method of providing a cardiac arrest emergency program of claim 17, wherein:

the step of developing said emergency program further includes assisting in complying with applicable laws relating to the use of automatic external defibrillators; and the step of supporting said emergency program further includes updating the program to respond to any new laws or changes in the applicable law.

20. The method of providing a cardiac arrest emergency program of claim 17, wherein:

the step of developing said emergency program further includes selecting personnel to serve as liaisons with emergency medical specialists who are called to the customer's premises; and the step of implementing said emergency program further includes training the customer's personnel regarding proper use of the at least one automatic external defibrillator.

21. The method of providing a cardiac arrest emergency program of claim 17, wherein:

the step of supporting said emergency program further includes providing a public relations support plan that assists in informing the public of the customer's implementation of the emergency program to promote the goodwill of the customer's business.

22. The method of providing a cardiac arrest emergency program of claim 17, wherein:

the step of supporting said emergency program further includes providing an automatic external defibrillator usage review in the event of a cardiac incident.

23. The method of providing a cardiac arrest emergency program of claim 17, wherein:

the step of supporting said emergency program further includes conducting periodic quality assurance inspections to ensure the proper operation of the at least one automatic external defibrillator.

24. The method of providing a cardiac arrest emergency program of claim 17, further comprising the step of:

collecting a fee from the customer for developing, implementing and supporting said emergency program.

* * * * *